(12) United States Patent
Kugelmann et al.

(10) Patent No.: US 9,066,888 B2
(45) Date of Patent: Jun. 30, 2015

(54) PLASTER CAUSING REDUCED SKIN IRRITATION

(75) Inventors: Heinrich Kugelmann, Aachen (DE);
Johannes Bartholomäus, Aachen (DE);
Rasoul Sedaghat Kerdar, Nürnberg (DE)

(73) Assignee: Gruenenthal GmbH, Aachen (DE)

( * ) Notice: Subject to any disclaimer, the term of this patent is extended or adjusted under 35 U.S.C. 154(b) by 2009 days.

(21) Appl. No.: 11/509,612

(22) Filed: Aug. 25, 2006

(65) Prior Publication Data

US 2007/0042028 A1  Feb. 22, 2007

Related U.S. Application Data

(63) Continuation of application No. PCT/EP2005/002032, filed on Feb. 25, 2005.

(30) Foreign Application Priority Data

Feb. 26, 2004  (DE) .......................... 10 2004 009 903

(51) Int. Cl.
| | | |
|---|---|---|
| A61F 13/00 | (2006.01) | |
| A61K 9/70 | (2006.01) | |
| A61L 15/44 | (2006.01) | |
| A61K 47/34 | (2006.01) | |

(52) U.S. Cl.
CPC ............... *A61K 9/7084* (2013.01); *A61F 13/00* (2013.01); *A61F 2013/00387* (2013.01); *A61F 13/00063* (2013.01); *A61L 15/44* (2013.01); *A61K 47/34* (2013.01)

(58) Field of Classification Search
USPC ........................................................ 424/449
See application file for complete search history.

(56) References Cited

U.S. PATENT DOCUMENTS

| | | | | |
|---|---|---|---|---|
| 4,756,710 | A * | 7/1988 | Bondi et al. ................. | 424/449 |
| 5,059,189 | A * | 10/1991 | Cilento et al. ................ | 604/307 |
| 5,232,702 | A * | 8/1993 | Pfister et al. ................. | 424/448 |
| 5,238,933 | A * | 8/1993 | Catz et al. ................... | 514/236.2 |
| 6,018,092 | A * | 1/2000 | Dunshee ....................... | 602/54 |
| 6,197,845 | B1 * | 3/2001 | Janssen et al. ................ | 523/111 |
| 2003/0175328 | A1 | 9/2003 | Shefer et al. | |
| 2004/0213819 | A1 * | 10/2004 | Albrecht ....................... | 424/401 |
| 2005/0208116 | A1 | 9/2005 | Stefano et al. | |

FOREIGN PATENT DOCUMENTS

| | | |
|---|---|---|
| DE | 37 14140 A1 | 11/1988 |
| DE | 268 397 A5 | 5/1989 |
| DE | 689 10 520 T2 | 4/1994 |
| DE | 42 41 874 A1 | 6/1994 |
| DE | 195 03 336 | 8/1996 |
| DE | 199 11 262 A1 | 9/2000 |
| DE | 199 09 493 C1 | 11/2000 |
| DE | 100 54 479 A1 | 5/2002 |
| DE | 100 56 010 A1 | 5/2002 |
| DE | 101 21 471 A1 | 11/2002 |
| EP | 0 416 137 A1 | 3/1991 |
| EP | 0 535 237 A1 | 4/1993 |
| EP | 0 607 434 A1 | 7/1994 |
| EP | 0 760 238 A1 | 3/1997 |
| EP | 1 503 743 B1 | 1/2007 |
| FR | 2 781 667 A1 | 2/2000 |
| JP | 06 256183 | 9/1994 |
| JP | 08 319234 | 12/1996 |
| WO | WO 97/48387 | 12/1997 |
| WO | WO 99/26572 | 6/1999 |
| WO | WO 0074616 A1 * | 12/2000 |
| WO | WO 01/26572 A1 | 4/2001 |
| WO | WO 01/43717 | 6/2001 |
| WO | WO 2005/082428 A2 | 9/2005 |

OTHER PUBLICATIONS

Bauer K.H. et al., "3 Transdermale Therapeutische Systeme (TTS)", Pharmazeutische Technologie (Pharmaceutical Technology), pp. 381-383.
Keipert, Prof. Dr. S., "Ophthalmika:etablierte Arznelformen und neue Konzepte", Pharmazeutische Technologie: Moderne Arzneiformen (Pharmaceutical Technology: Modern Pharmaceutical Forms), Chapter 8, pp. 77-98.
R. H. Müller et al., "Pharmazeutische Technologie: Moderne Arzneiformen", 1996, (nineteen (19) pages).
Verpackungs-Rundschau, "Bis zu sechs Bahnen; Pflaster herstellen und verpacken", Apr. 2002, pp. 83-84.
Bauer K.H. et al., "3 Transdermale Therapeutische Systeme (TTS)", Pharmazeutische Technologie (Pharmaceutical Technology), pp. 381-383, 1997.
Keipert, Prof. Dr. S., "Ophthalmika:etablierte Arzneiformen und neue Konzepte", Pharmazeutische Technologie: Moderne Arzneiformen (Pharmaceutical Technology: Modern Pharmaceutical Forms), Chapter 8, pp. 77-98, 1998.
"Testoderm® TTS," Physician's Desk Reference, Edition 55, pp. 535-538, 2001.

* cited by examiner

*Primary Examiner* — James Rogers
(74) *Attorney, Agent, or Firm* — Crowell & Moring LLP

(57) ABSTRACT

A plaster containing an active ingredient for the transdermal administration of a pharmaceutical active ingredient, having a removable protective film and an adhesive layer. The plaster includes at least one compound that is contained in the adhesive layer or lies adjacent the adhesive layer between the adhesive layer and the removable protective film and that can be applied to the skin to at least reduce skin irritation.

7 Claims, No Drawings

PLASTER CAUSING REDUCED SKIN IRRITATION

CROSS REFERENCE TO RELATED APPLICATIONS

This application is a continuation of international patent application No. PCT/EP2005/002032, filed Feb. 25, 2005, designating the United States of America and published in German on Sep. 9, 2005 as WO 2005/082428, the entire disclosure of which is incorporated herein by reference. Priority is claimed based on Federal Republic of Germany patent application No. DE 10 2004 009 903.0, filed Feb. 26, 2004.

BACKGROUND OF THE INVENTION

The present invention relates to an active substance plaster for transdermal administration of a pharmaceutically active substance, comprising at least one removable protective film and an adhesive layer, characterized in that the plaster has at least one compound within the adhesive layer or adjacent the adhesive layer between the adhesive layer and the removable protective film, which compound is transferable to the skin surface and at least partially reduces skin irritation.

It is known that intense contact of plasters with the skin, especially in the case of dry or damaged skin of humans or animals, can lead to erythema, pustules, pruritus, or other manifestations of skin irritation. These skin reactions can occur in as many as 30% of plaster users to various extents. The result is an only moderate acceptance of these products, which can mean a premature termination of treatment.

The problem has therefore been to provide an active substance plaster not suffering from the drawbacks found in the prior art, in that it produces less skin irritation.

SUMMARY OF THE INVENTION

This problem has now been solved by preparing the active substance plaster of the invention for the transdermal release of an active pharmaceutical substance, consisting of at least one removable protective film layer and an adhesive layer, characterized in that the plaster comprises at least one compound within the adhesive layer or adjacent the adhesive layer between the adhesive layer and the removable protective film, which compound is transferable to the skin surface and at least partially reduces skin irritation.

Due to its design, the plaster of the invention has the advantage that the compound which at least partially reduces skin irritation is placed directly on the skin surface upon application of the plaster, thereby preventing skin irritation from the onset of the therapy, particularly when the irritation reducing compound or substance is present between the adhesive layer and the protective layer.

The compound that is transferable to the skin surface for reduction or prevention of skin irritations is preferably a skin friendly compound selected from the group consisting of paraffins, silanols, silicones, silicone derivatives, monohydric, dihydric or polyhydric alcohols, natural or synthetic lipids, natural or synthetic waxes, natural or synthetic fats, fatty acids and/or fatty alcohols, natural or synthetic oils, natural or synthetic polymers, starches, proteins, vitamins, compounds with antiphlogogenic or antiphlogistic characteristics, compounds for growth prevention of phlogogenic microorganisms, compounds with anesthetizing characteristics, compounds that are effective as radical scavengers, enzymes, herbal extracts, preservatives, and mixtures thereof consisting of at least two compounds of one class or at least two compounds of different classes. If glycerin is used as a skin friendly, in particular skin smoothing, compound, this is used only in combination with at least one further compound from a different class, preferably at least one compound selected from the preferably used compounds that at least partially reduce skin irritations as mentioned below.

As used herein, the designation "compound that at least partially reduces skin irritations" includes combinations of the compounds stated as having the desired effect according to the invention.

Suitable silicone derivatives are preferably substituted or unsubstituted polysiloxanes optionally in admixture with acrylate polymers.

Suitable compounds having antiphlogogenic or antiphlogistic characteristics are preferably allantoin, dexpanthenol, bisabolol, chamazulene, aescin, basic aluminum acetate/tartrate, zinc oxide, tannin, melatonin, balsam of Peru, bismuth gallate, derivatives and/or salts thereof, corticoids, such as, preferably, hydrocortisone, betamethason, fluocinolone acetonide, fluocinonide, prednisolone, methyl prednisolone, triamcinolone, flumetasone, clobetasol, fluprednides, alclometasone, prednicarbate, mometasone, fluticasone, halcinonid, clocortolone, diflucortolone, desoximetasone and/or derivatives thereof, and also antihistamines, such as, preferably, diphenhydramine, dimetindene, isoprenalin, clemastin, bamipine, and derivatives and/or salts thereof.

Compounds for growth prevention of antiphlogogenic microorganisms are preferably benzalkonium chlorides such as, for example, benzethonium chloride, methylhydroxybenzoate, propylhydroxybenzoate, chlorohexidine, dequalinium chloride, clioquinol, sorbic acid, derivatives and/or salts thereof, antiseptics such as, preferably, povidon iodine, iodoform, thymol, tyrothricin, chlorocresol, salicylic acid, ethacridin or polidocanol, derivatives and/or salts thereof and antiphlogogenic agents such as, preferably, framycetin, neomycin, gentamicin, nystatin, erythromycin, tetracyclin, chlorotetracycline, oxytetracyclin, fusidic acid, metronidazole, bacitracin zinc, miconazole, amphotericin B, derivatives and/or salts thereof Compounds with anesthetizing characteristics are preferably benzocaine, lidocaine, tetracaine, prilocaine, mepivacaine, and derivatives and/or salts thereof.

Suitable vitamins are preferably Vitamin A derivatives, preferably retinol acetate or retinol palmitate, Vitamin B derivatives, Vitamin C derivatives, such as, for example, the respective palmitates, Vitamin D derivatives, preferably colecaliciferol or Vitamin E derivatives, preferably α-tocopherol acetate.

Suitable enzymes are preferably superoxide dismutases or catalases.

Suitable herbal extracts are preferably extracts of plants such as for example aloe vera, arnica, basil, wild plum (Lat.: *Prunus spinosa*), greater burdock (Lat.: *Arctium lappa*), pot marigold (Lat.: *Calendula officinalis*), camellia (Lat.: *Camellia oleifera*), clary (Lat.: *Salvia clarea*), German chamomile (Lat.: *Matricaria chamomilla*), comfrey (Lat.: *Symphytum officinale*), echinacea (Lat.: *Echinacea angustifolia*), cucumber (Lat.: *Cucumis Sativus*), euphrasia (Lat.: *Euphrasia officinalis*), ginseng, green tea, lavender, chamomile (Lat.: *Chamomilla recutita and Matricaria chamomilla*), peppermint (Lat.: *Mentha piperita*), mugwort, nutmeg, avena (Lat.: *Avena sativa*), sandal wood, safflower (Lat.: *Carthamus tinctorius*), soy, melaleuca (Lat.: *Melaleuca alternifolia*), vetiver grass (Lat.: *Vetiveria zizanioides*), violet, licorice (Lat.: *Glycyrrhiza glabra*) and/or witch hazel (Lat.: *Hamamelis*).

Of the aforementioned compounds preferably those are suitable that also have a skin smoothing action. Suitable as a compound for at least partially reducing skin irritations is at least one skin smoothing compound or substance selected from the group consisting of glycerin, chitosane, hydroxypropylmethylcellulose, oetearyl octanoate, vitamin E, coconut fat, arachis oil, soybean oil, and *Butyrospermum parkii* (shea butter), whereas hydrophilic compounds such as glycerin are only used in combination with one of the above mentioned skin soothing compounds.

Particularly preferred and suitable is at least one skin friendly compound selected from the group consisting of polymeric compounds, preferably fluorinated polyethers, more preferably polyperfluoro-methylisopropyl ether, or silicone derivatives; compounds with antiphlogenic or antiphlogistic characteristics, preferably corticoids or antihistamines; compounds for prevention of growth of phlogogenic microorganisms, preferably antiseptics; or anti-infective agents, and compounds effective as free-radical scavengers, preferably N-acyl ethanolamine.

The active substance plaster according to the invention may be constructed according to the reservoir or matrix system (Bauer K. H., Frömming K.-H., Führer C, Pharmazeutische Technologie (Pharmaceutical Technology), Pages 381-383; Müller R. H., Hildebrand G. E., Pharmazeutische Technologie: Moderne Arzneiformen (Pharmaceutical Technology: Modern Pharmaceutical Forms), Chapter 8.

In the matrix-system the plaster containing the active substance can preferably consist of a substrate layer, a layer containing the active substance, an adhesive layer, and a removable protective film. The layer containing the active substance can at the same time be the adhesive layer, in which the active substance is present in a matrix in dissolved and/or dispersed form together with the adhesive.

Preferably, the adhesive layer and the layer containing the active substance are separate layers, whilst the adhesive may be applied to the layer containing the active substance over the entire area thereof or only a portion thereof or only a circular portion thereof.

If the plaster according to the invention is constructed according to the reservoir system, the adhesive layer may be applied to the entire area of, or as a ring surrounding, the reservoir membrane of the reservoir system.

If the plaster according to the invention does not contain a separate layer containing an active substance, the adhesive layer may be applied to the substrate layer entirely or partially, for example in segments, with or without areas containing active substances.

At least one compound or substance which at least partially reduces skin irritations and which is transferable to the skin surface is present as a component of the adhesive layer and/or on the adhesive layer between the adhesive layer and the protective film of the plaster of the invention.

If the compound is present in the adhesive layer, it can be dissolved or dispersed therein. If the adhesive layer is at the same time the active substance layer, the compound will be present in the adhesive layer in dissolved and/or dispersed form together with the active ingredient. The compound for reducing skin irritations is preferably disposed within the adhesive layer to correspond to the configuration of the areas of the adhesive layer that contain the active substance.

Alternatively, the compound or substance may be present only in a subregion of the adhesive layer such that this subregion forms a reservoir for only the skin friendly compound.

Preferably, the compound or substance which at least partially reduces skin irritations and which is transferable to the skin surface, is located adjacent to the adhesive layer, between the adhesive layer and the protective film, in which case, upon removing the protective film, the compound will initially remain on the adhesive layer, but at the instant of application it will be immediately transferred to the skin surface. Preferably the location of the skin friendly compound corresponds to the location of the adhesive layer in the plaster of the invention.

If the compound which is transferable to the skin surface and which at least partially reduces skin irritations is present adjacent to the adhesive layer between the latter and the protective film, it can be applied evenly to conform to the location of the adhesive layer, preferably covering the entire surface in the form of a film or layer, or selectively, for instance in multiparticular form.

If the compound which at least partially reduces skin irritations and which is transferable to the skin surface is present in multiparticular form, it can preferably be present in micro or nano capsules, micro or nano particles, or liposomes.

As already mentioned, the compound or substance which at least partially reduces skin irritations and which is transferable to the skin surface, is preferably present in the form of a layer having a preferred thickness of <5 µm, more preferably from 0.5-2 µm and disposed between the removable protective film and the adhesive layer.

It will be apparent to those skilled in the art that the compound that is transferable to the skin surface and that at least partially reduces skin irritations, present either within the adhesive layer or adjacent to the adhesive layer, should be present in only an amount such as will not, or only slightly, interfere with the adhesive action of the adhesive layer, but will still have the desired effect.

Preferably, pressure-sensitive adhesives are used for the adhesive layer of the plaster of the invention. Examples of suitable adhesives are polymers such as polyacrylates, polyvinyl ethers, polyisobutylene (PIB), styrene/isoprene copolymers or butadiene/styrene copolymers or polyisoprene rubber. Other suitable adhesives are silicone adhesives such as, for example, optionally cross-linked polydimethylsiloxanes. Resins such as, for example, polyesters of glycinen, glycerin, or pentaerythrol, or hydrocarbon resins such as polyterpene are also suitable. Acrylate-substrate layerd adhesives are produced by polymerization of acrylates, methacrylates, alkyl acrylates and/or alkyl methacrylates, optionally with a further $\alpha,\beta$-unsaturated monomer such as acrylamide, dimethylacrylamide, dimethylaminoethyl acrylate, hydroxyethyl acrylate, hydroxypropyl acrylate, methoxyethyl acrylate, methoxyethyl methacrylate, acrylonitrile, and/or vinyl acetate.

The adhesive layer may also contain additional adjuvants, such as plasticizers, for example phthalates such as dibutyl phthalates, mineral oils, esters of citric acid, or esters of glycerin, skin penetration enhancers, fillers (such as zinc oxide or silica), cross linkers, preservatives, and/or lipophilic solvents.

The substrate layer, or top layer, of the plaster is preferably impermeable and inert to the substances present in the layer containing the active substance and to the substances in the adhesive layer, especially to the active substance present therein, and can consist of polyesters, for example polyethylene phthalates, polyolefins, such as polyethylenes, polypropylenes, or polybutylenes, polycarbonates, polyethylene oxides, polyterephthalates such as polyethylene terephthalates, polyurethanes, polystyrenes, polyamides, polyimides, polyvinyl acetates, polyvinyl chlorides, and/or polyvinylidene chlorides, copolymers such as acrylonitrile/butadiene/styrene copolymer containing fibers, textile fibers, and/or mixtures thereof, which may be metallized or pigmented if necessary. The substrate layer may also consist of a combination of a metal foil and a polymeric layer.

The plaster according to the invention is suitable for transdermal administration of any systemic, ie transdermally effective, pharmaceutically active substance. Preferably the plaster according to the invention is suitable for transdermal (systemic) release of at least one pharmaceutically active substance from the group consisting of analgetics, local anesthetics, hormones, contraceptives, vaccines, immune modulators, anti-allergic agents, antihistamines, cardiac agents, antihypertonics, psychotropics, anti-rheumatic agents, and enzymes. It is particularly suitable for transdermal administration of opioids, such as, for example, buprenorphine, tentanyl, or morphine.

The required dosage for transdermal administration of the active substance is known to the person skilled in the art and is dependent on the duration of the therapy, among other factors.

A active substance matrix layer of the plaster according to the invention can, along with a pharmaceutical agent, contain matrix forming polymers, plasticizers, permeation enhancers, lipophilic solvents, cross-linking agents, preservatives, emulsifiers, and thickening agents, together with the adhesive, if present.

Matrix forming polymers can usually be film forming polymers such as, for example, hydroxypropylcellulose, carboxymethylcellulose, polyethylenes, chlorinated polyethylenes, polypropylenes, polyurethanes, polycarbonates, polyacrylic acid esters, polyacrylates, polymethacrylates, polyvinyl alcohols, polyvinyl chlorides, polyvinylidene chlorides, polyvinylpyrrolidones, polyethylene therephthalates, polytetrafluoroethylenes, ethylene/propylene copolymers, ethylene/ethyl acrylate copolymers, ethylene/vinyl acetate copolymers, ethylene/vinyl alcohol copolymers, ethylene/vinyloxyethanol copolymers, vinyl chloride/vinyl acetate copolymers, vinylpyrrolidone/ethylene/vinyl acetate copolymers, rubbers, rubber-like synthetic homopolymers, copolymers or block polymers, silicones, silicone-derivatives such as polysiloxane/polymethacrylate copolymers, cellulose derivatives such as ethyl cellulose or cellulose ether, and/or mixtures thereof. If the layer containing the active substance is at the same time the adhesive layer, it preferably contains at least one of the above mentioned adhesives along with at least one of the listed polymers.

Suitable lipophilic solvents are N-methyl-2-pyrrolidone, lauryl pyrrolidone, triacetin, diethylene glycol monoethyl ether, and derivatives of fatty acids or fatty alcohols.

If the active substance plaster is constructed according to the reservoir system, the reservoir membrane can consist of inert polymers such as, for example, polyethylenes, polypropylenes, polyvinyl acetates, polyamides, ethylene/vinyl acetate copolymers, and/or silicones. The reservoir membrane allows for a controlled release of the active substance.

The reservoir containing the active substance can also contain a solvent, such as, for example, water, ethanol, 1-propanol, isopropanol, a low molecular weight, polyhydric alcohol, for example propylene glycol or glycerin, or an ester, such as isopropyl myristate, or mixtures thereof, in conventional amounts.

Preservatives for the matrix or reservoir containing the active substance can be antioxidants, such as vitamin E, butylhydroxytoluene, butylhydroxyanisol, ascorbic acid, ascorbyl palmitate, and/or chelating agents, such as disodium methylenediamine tetraacetic acid, potassium nitrate, or sodium nitrate, in conventional amounts.

The matrix or reservoir containing the active substance can also contain known and conventional permeation enhancers and/or viscosity enhancing agents in the matrix or reservoir containing the active substance, such as, for example, cellulose derivatives or natural or synthetic rubbers. The pharmaceutical agent in the plaster according to the invention is preferably present in a matrix layer.

The release of active substance from the plaster of the invention is preferably controlled.

The plaster according to the invention can also contain, in one or more layers and in conventional amounts, at least one plasticizer selected from the group consisting of long-chain alcohols such as dodecanol, undecanol, octanol, esters of carboxylic acid with polyethoxylated alcohols, diesters of aliphatic dicarboxylic acids such as adipic acid, and medium-chain triglycerides of caprylic acid and/or capric acid, coconut oil, polyhydric alcohols such as for example propane-1,2-diol, esters of polyhydric alcohols such as glycerin with levulic acid or caprylic acid, and etherified polyhydric alcohols.

The protective film can consist of polyethylene, polyesters, polyethylene terephthalate, polypropylene, polysiloxane, polyvinyl chloride, or polyurethane or optionally of treated paper fibers, such as, for example, cellophane, and optionally contain a layer of silicone, fluorosilicone, or fluorocarbon.

The production of the plasters is carried out by known manufacturing techniques for plasters comprising process steps such as laminating, die cutting, delaminating, uncoiling, cutting, recoiling, mounting or metering (see Verpackungs-Rundschau 4/2002, 83-84).

The plaster of the invention can be applied to humans or animals, and skin irritations that are caused due to usage of plaster largely avoided.

EXAMPLES

Example 1

A matrix plaster was tested, both with and without the skin irritation-reducing layer, containing 0.5% by weight of capsaicin as active ingredient, and an adhesive layer substrate layerd on a polyacrylate and disposed over the active ingredient layer, and having, where applicable, a layer of polyperfluoromethylisopropyl ether having a thickness of approximately 1 μm over the adhesive layer, between the adhesive layer and protective film.

Five individuals tested plasters with and without a skin irritation-reducing agent, by placing the respective plaster having a size of 2×2 cm for a period 3 days on a hairless area of the forearm, after removing the protective foil. Three days later the plasters were removed and the skin irritation was assessed immediately, and again after a further 24 hours. Results are shown in the following table:

| Person | Plaster without the use of a layer of polyperfluoromethylisopropyl ether | | Plaster with the use of a layer of polyperfluoromethylisopropyl ether | |
| --- | --- | --- | --- | --- |
| | after 3 d | after 4 d | after 3 d | after 4 d |
| 1 | +++ | +++ | (+) | − |
| 2 | ++ | +++ | − | − |
| 3 | +++ | ++ | − | − |
| 4 | ++++ | +++ | (+) | − |
| 5 | ++ | +++ | − | − |

− = no skin irritation
(+) = scarcely visible skin irritation
+ = weak skin irritation
++ = spots of strong skin irritation
+++ = strong irritation
++++ = strong irritation with pustules The test results confirm that the plaster having a layer of skin irritation-preventing compound does indeed largely prevent such irritations.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. An active substance plaster for transdermal administration of at least one pharmaceutically active substance, said plaster comprising a layer containing at least one pharmaceutically active substance to be administered, an adhesive layer separate from the pharmaceutically active substance-containing layer, a removable protective film and a skin irritation reducing-compound that can be transferred to the surface of the skin, wherein said skin irritation-reducing compound is present in the form of another layer separate from the pharmaceutically active substance-containing layer and the adhesive layer, disposed adjacent said adhesive layer and between said adhesive layer and said removable protective film, and distributed over the entire surface of said adhesive layer, wherein the skin irritation-reducing compound is polyperfluoromethylisopropyl ether or N-acyl ethanolamine.

2. A plaster according to claim 1, wherein said plaster further comprises a substrate layer.

3. A plaster according to claim 1, wherein the skin irritation-reducing compound is uniformly distributed over the surface of the adhesive layer.

4. A plaster according to claim 1, wherein the skin irritation-reducing compound is present in such an amount that the adhesive action of the adhesive layer is substantially unimpaired.

5. A plaster according to claim 1, wherein said pharmaceutically active substance is selected from the group consisting of analgesics, hormones, contraceptives, vaccines, immunomodulators, anti-allergic agents, cardiac agents, psychotropic agents, antirheumatic agents, and enzymes.

6. A plaster according to claim 5, wherein the pharmaceutically active substance comprises at least one opioid analgesic.

7. A plaster according to claim 6, wherein the opioid analgesic is buprenorphine.

* * * * *